United States Patent [19]

Boardman et al.

[11] Patent Number: 5,580,901
[45] Date of Patent: Dec. 3, 1996

[54] PHARMACEUTICAL COMPOSITIONS OF AMETHOCAINE FREE BASE

[75] Inventors: David G. Boardman, Harold Wood; Kevin Maughan, Welwyn, both of United Kingdom

[73] Assignee: T. J. Smith & Newphew Limited, England

[21] Appl. No.: 287,470

[22] Filed: Aug. 8, 1994

Related U.S. Application Data

[63] Continuation of Ser. No. 927,308, Sep. 25, 1992, abandoned.

[30] Foreign Application Priority Data

Jan. 30, 1991 [GB] United Kingdom .................. 9101986
Jan. 29, 1992 [WO] WIPO .................... PCT/GB92/00170

[51] Int. Cl.$^6$ ................................................ A61K 31/24
[52] U.S. Cl. ............................................................ 514/536
[58] Field of Search ................................................ 514/536

[56] References Cited

U.S. PATENT DOCUMENTS

| | | | |
|---|---|---|---|
| 1,889,645 | 11/1932 | Eisler et al. . | |
| 1,954,152 | 4/1934 | Streitwolf et al. | 167/52 |
| 2,132,351 | 10/1938 | Dorsbach et al. | 167/52 |
| 3,272,700 | 9/1966 | Shupe | 167/52 |
| 4,148,917 | 4/1979 | Smith | 514/536 |
| 4,181,725 | 1/1980 | Voorhees et al. | 424/258 |
| 4,248,855 | 2/1981 | Blank et al. | 424/19 |
| 4,474,751 | 10/1984 | Haslam et al. | 424/78 |
| 4,474,753 | 10/1984 | Haslam et al. | 424/78 |
| 4,478,822 | 10/1984 | Haslam et al. | 424/78 |
| 4,529,601 | 7/1985 | Broberg et al. | 514/626 |
| 4,562,060 | 12/1985 | Broberg et al. | 424/28 |
| 4,599,354 | 7/1986 | Shulman | 514/530 |
| 4,686,211 | 8/1987 | Hara et al. | 514/148 |
| 4,748,022 | 5/1988 | Busciglio | 424/195.1 |
| 5,002,974 | 3/1991 | Geria | 514/782 |
| 5,120,545 | 6/1992 | Ledger et al. | 424/449 |
| 5,149,320 | 9/1992 | Dhaliwal et al. | 604/49 |
| 5,192,802 | 3/1993 | Rencher | 514/535 |
| 5,209,724 | 5/1993 | Dhaliwal et al. | 604/49 |
| 5,234,957 | 8/1993 | Mantelle | 514/772.6 |
| 5,298,528 | 3/1994 | Evers | 514/626 |
| 5,314,915 | 5/1994 | Rencher | 514/535 |
| 5,332,576 | 7/1994 | Mantelle | 424/443 |

FOREIGN PATENT DOCUMENTS

| | | |
|---|---|---|
| 0336901 | 10/1989 | European Pat. Off. . |
| 2016456 | 5/1970 | France . |
| 2163956 | 3/1986 | United Kingdom ......... A61K 31/245 |
| 8809169 | 12/1988 | WIPO ............................. A61K 9/70 |

OTHER PUBLICATIONS

Zhou et al., *Chemical Abstracts*, vol. 105, No. 10, 8 Sep. 1986, abstract no. 85036a, p. 399.

*Primary Examiner*—Marianne M. Cintins
*Assistant Examiner*—William R. A. Jarvis
*Attorney, Agent, or Firm*—Graham & James LLP

[57] ABSTRACT

A storage stable composition for topical anesthesia comprising amethocaine free base, an aqueous gelling agent, and from 1 to 30% by weight of a pharmaceutically acceptable salt is disclosed.

14 Claims, No Drawings

PHARMACEUTICAL COMPOSITIONS OF AMETHOCAINE FREE BASE

This application is a continuation of U.S. application Ser. No. 07/927,308, filed Sep. 25, 1992, now abandoned.

The present invention relates to pharmaceutical compositions and more particularly to compositions useful for topical anaesthesia.

Amethocaine (2-dimethylaminoethyl p-butyl aminobenzoate) is used in topical preparations to provide percutaneous anaesthesia. Topical percutaneous anaesthetic compositions containing amethocaine base which are the form of aqueous gels are disclosed in GB-2163956-A.

Although amethocaine base is but sparingly soluble in water, dispersions in water will have pH values typically from pH 8 to 11 and under these pH conditions have a high rate of hydrolysis. It has been proposed to stabilise amethocaine by the addition of acids to produce salts and it has been demonstrated that salts such as the hydrochloride exhibit maximum stability at pH values of between pH 3 and 4. However, use of amethocaine salts for storage stability denies the user the benefits which accrue by the use of amethocaine free base.

We have now found that hydrated amethocaine base may be formulated into storage stable gel formulations suitable for percutaneous anaesthetic use.

According to the present invention there is provided a pharmaceutical composition suitable for percutaneous anaesthesia, comprising amethocaine, an aqueous gelling agent and a pharmaceutically acceptable salt in an amount of from 1 to 30% by weight of the composition wherein the pH of the composition is not less than pH 7.0.

The present invention provides a process for the preparation of such anaesthetic compositions which comprises mixing together amethocaine, a gelling agent and a pharmaceutically acceptable salt in an amount of from 1 to 30% by weight of the composition, and maintaining the pH of the mixture at a pH of not less than pH 7.0.

The concentration of salt employed is that which will reduce the aqueous solubility of amethocaine base significantly, for example from 25% to 100% when adjusted to a buffered pH range of 7.0–10.0. Generally salt concentrations of from 1 to 30% will fulfil this criterion. Aptly the salt concentration will be not less than 5% w/w. The salt concentration need not normally exceed about 25% w/w. Thus aptly the salt will be present in an amount of from 5 to 25%, more suitably less than about 10%. Typically the salt concentration will be about 5%.

The compositions of the present invention will have a pH value of pH 7.0 or above. pH values within this range may be achieved by the use of suitable buffering agents. Aptly the pH range will be less than 10 and more aptly will be in the range of pH 7.5–8.5. More aptly the pH range will be from 7.4 to 8.4 and preferably will be about pH 7.7. The buffering agents which may be employed in the practice of the present invention may include any of those known for this purpose. Apt buffering agents for use in the present invention include inorganic and organic buffering agents such as the phosphate, borate and citrophosphate buffers.

The amethocaine is present in the composition, as the hydrated free base in amounts generally greater than 1% by weight of the total composition. The amount of amethocaine generally need not exceed 10% w/w since amounts greater than this would not normally be expected to increase the anaesthetic effect. Aptly the amethocaine concentration will be from 1–10% w/w, more aptly from 2–6% w/w. Typically the amethocaine concentration will be about 4%.

The gelling agent employed in the composition of the invention may be any of those conventionally employed and which are stable under the pH conditions employed. The gelling agent should have suitable rheological properties for its intended use. Thus, it should have a shear-dependent viscosity high enough for it to maintain its physical integrity on storage and yet low enough to permit it to be filled into suitable dispensers to be expelled from the dispensers at the point of use and to be readily spread over the skin. Suitable gelling agents include methyl cellulose, hydroxy ethyl cellulose, carbomers and other pharmaceutically acceptable thickening agents such as xanthan gum.

The salts employed in the composition of the invention need to be both water soluble and either neutral or able to be buffered to a pH of 7.0 or above. The salts may contain organic or inorganic anions. Apt inorganic ions include sulphate, borate, phosphate, nitrate carbonte or halide. Apt organic anions will include acetate and citrate. The salt cation may be an alkali or alkaline earth metal or iron. Apt salts for use in the invention include sodium and potassium chlorides and other halides, and magnesium sulphate.

In preparing the compositions of the invention, the amethocaine maybe employed directly in the form of the free base. Alternatively the free base may be generated in situ by incorporating an amethocaine salt, eg. the hydrochloride and a suitable base eg. sodium hydroxide into the gel formulation. Some salt will be formed as a result of the reaction between the amethocaine salt and the base, which will contribute to the salt level in the formulation. Salts used as buffering agents in the gel formulations may also contribute to the total salt concentration in the gel formulation of the invention.

The composition of the present invention may be prepared and packaged under sterile conditions. Alternatively, suitable antimicrobial agents may be incorporated into the formulations as preservatives.

Aptly the composition of the present invention may be packaged in a dispenser, suitably a tube. Similarly, the dispenser is adapted to deliver unit dose quantities of the anaesthetic, for example the composition is packaged in a tube whose volume is equivalent to one unit dose.

Alternatively the compositions may be presented in the form of a dressing comprising a skin-conformable backing layer having on its skin facing surface, a skin contacting layer of a composition in accordance with the invention.

Aptly, the presentation may be in the form of an adhesive dressing wherein the skin contacting layer of anaesthetic composition is inset from the edges of the conformable body layer and the free area of the skin facing surface has a layer of adhesive thereon. Preferably, the anaesthetic layer is inset from all the edges of the backing layer and is surrounded by a layer of adhesive.

It is desirable to store the compositions of the invention at a temperature below the melting point of the hydrated amethocaine base (32° C.). Aptly the composition will be stored at temperatures greater than 5° C., more aptly the compositions of the invention will be stored at a temperature between 5° to 30° C. Suitably the compositions of the invention will be stored at a temperature of from 5° to 15° C.

The compositions of the invention have been shown to exhibit good storage stability with low amethocaine decomposition even at relatively high storage temperatures.

The compositions of the invention may be applied directly to the skin for inducing topical anaesthesia.

The invention will now be illustrated by the following Examples.

EXAMPLE 1

Three formulations were prepared as follows:

|  | 1 | 2 | 3 |
|---|---|---|---|
| Amethocaine Base (% w/w) | 4.0 | 4.0 | 4.0 |
| Hydroxyethyl cellulose (% w/w) | 1.5 | 1.5 | 1.0 |
| Sodium Chloride (% w/w) | — | — | 24.0 |
| Dionised Water (% w/w) | qs 100 | qs 100 | qs 100 |
| pH | 9.4 | 7.6 (buffered) | 9.4 |

Formulation 3 is an example of the invention. The other formulations are controls.

Samples of each formulation were then aged for 9 weeks at 5° C., 12° C. and 25° C. respectively, after which each sample was analysed using High Performance liquid chromotography to determine the percentage decomposition of the amethocaine to butyl p-amino benzoic acid. The results are given in the following table:

| Formulation | pH | % Decomposition | | |
|---|---|---|---|---|
| | | 5° C. | 12° C. | 25° C. |
| 1 | 9.4 | 1.1 | 1.93 | 7.97 |
| 2 | 7.6 | 0.76 | 0.90 | 4.68 |
| 3 | 9.4 | 0.38 | 0.28 | 0.32 |

It will be seen from the foregoing results that the stability of the amethocaine hydrate compositions in accordance with the present invention can be achieved at high pH values.

EXAMPLE 2

Gel compositions suitable for percutaneous anaesthesia were prepared by mixing the following:

| | |
|---|---|
| Amethocaine Hydrochloride | 4.55% w/w |
| Sodium Hydroxide | 0.605% w/w |
| Sodium Chloride | 5.0% w/w |
| Xanthan Gum | 1.0% w/w |
| Deionised water* | qs 100%* |

*a buffering agent was included to buffer the pH of the gel to pH 7.6.

The formulated gel exhibited satisfactory stability and rheological properties.

EXAMPLE 3

Other anaesthetic compositions derived from amethocaine hydrochloride were prepared according to the following formulations:

| | wt % of Composition | | | |
|---|---|---|---|---|
| | A | B | C | D |
| Amethocaine Hydrochloride | 4.6 | 4.6 | 4.6 | 4.6 |
| Sodium Hydroxide | 1.3 | 1.3 | 1.3 | 1.3 |
| Sodium Chloride | 5.0 | 5.0 | 10.0 | 10.0 |
| Xanthan Gum | 1.0 | 2.0 | 1.0 | 2.0 |
| Potassium Dihydrogen Phosphate | 2.9 | 2.9 | 2.9 | 2.9 |
| Deionised water | qs 100 | qs 100 | qs 100 | qs 100 |
| pH | 7.6 | 7.5 | 7.5 | 7.7 |
| % decomposition | 3.1 | 2.9 | 1.9 | 1.9 |

Each of the compositions were then subjected to ageing at 25° C. for 9 weeks and analysed for decomposition products as described in Example 1 and are also reported above.

These results further demonstrate the effect of inclusion of sodium chloride with Formulations C and D containing 10% sodium chloride showing only 1.9% decomposition of amethocaine compared to about 3% decomposition in formulations A and B containing 5% sodium chloride. A change in the concentration of Xanthan Gum from 1% to 2% did not result in a change in the rate of decomposition, indicating that the viscosity of the formulation does not influence the rate of decomposition of amethocaine.

EXAMPLE 4

Gel compositions A–I were made up according to the formulations shown in the following table and tested for storage stability over a period of 9 weeks at a temperature of 25° C. With the exception of Composition A, the formulations were either pH adjusted (formulation B to D) or were buffered to about pH 7.5. The chemical stability was determined by measuring the decomposition to butyl p-amino benzoic acid, as described in Example 1.

Compositions D to G are examples of the invention whereas compositions A to C, H and I are included for control purposes.

| Reference | A | B | C | D | E | F | G | H | I |
|---|---|---|---|---|---|---|---|---|---|
| Amethocaine Base | 4.0 | 4.0 | 4.0 | 4.0 | 4.0 | 4.0 | 4.0 | 2.0 | |
| Amethocaine HCl | | | | | | | | | 2.3 |
| NaOH | | | | | | | | 0.5 | 0.7 |
| HEC* | 1.5 | 1.5 | 1.5 | 1.5 | | | | | |
| Xanthan Gum | | | | | 1.0 | 1.0 | 1.0 | 1.0 | 1.0 |
| THMA** | | | | | 2.0 | | 2.0 | | |
| MgSO$_4$ | | | | | 20.0 | | | | |
| NaCOOCH$_3$ | | | | | | 20.0 | | | |
| NaCl | | 0.5 | 5.0 | | | | 10.0 | | |
| KH$_2$PO$_4$ | | | | | 2.0 | | | 2.9 | 2.9 |
| pH | 9.1 | 7.5 | 7.5 | 7.5 | 7.5 | 7.5 | 7.0 | 7.6 | 7.6 |
| % decomposition | 7.5 | 7.8 | 7.2 | 4.0 | 2.0 | 0.8 | 1.9 | 9.5 | 8.9 |

*Hydroxyethylcellulose
**Tris(hydroxymethyl)aminomethane

Formulations A to D were designed to examine the effects of adjustment of pH and inclusion of salt on gel composition exemplified by Patent Specification GB 2163956-A (corresponds to formulation A). The data on rate of decomposition show that whilst adjustment of pH to 7.5 and inclusion of salt at 0.5% level did not lead to a reduction in the decomposition rate, presence of salt at 5% level (formulation D) resulted in a significant reduction in the degree of decomposition of amethocaine.

Formulations E and F are examples of the current invention showing markedly reduced levels of decomposition in presence of salts other than sodium chloride, namely magnesium sulphate and sodium acetate, respectively. Formulations E and G also illustrate the use of an organic buffer (Tris buffer) instead of the phosphate buffer to achieve a pH of about 7.5. Furthermore, a comparison of the decomposition rate in formulation G, which was buffered using Tris buffer and contained 10% sodium chloride with that in formulation C of Example 2 which also contained 10% sodium chloride but was buffered using the phosphate buffer shows that the nature of buffer had no demonstratable effect on the rate of decomposition of amethocaine. Thus the pH and presence of salt were shown to be the critical factors for reducing the rate of decomposition of amethocaine, in accordance with the invention.

Formulations H and I were prepared with a final concentration of amethocaine base of 2% to illustrate the effects of starting with amethocaine base or generating the base in situ by neutralising amethocaine hydrochloride with sodium hydroxide in its formulation. The small amount (about 0.5%) of sodium chloride generated in the latter formulation was shown not to have a significant effect on the rate of decomposition of amethocaine.

We claim:

1. A pharmaceutical composition suitable for percutaneous anaesthesia, comprising (1) amethocaine free base, (2) an aqueous gelling agent and (3) from 1 to 30% by weight of a pharmaceutically acceptable salt, having an alkali or alkaline earth metal cation, wherein the pH of the composition is not less than pH 7.0.

2. A composition as claimed in claim 1 wherein the salt anion comprises chloride, sulphate, phosphate, borate, acetate or citrate.

3. A composition as claimed in claim 1 wherein the salt is present in an amount of from 5 to 25% by weight of the composition.

4. A composition as claimed in claim 1 wherein a portion of the salt component is provided by a buffering agent.

5. A composition according to claim 1 wherein the pH is maintained at about pH 7.7.

6. A composition according to claim 1 wherein the gelling agent comprises methyl cellulose, hydroxyethyl cellulose, a carbomer or xanthan gum.

7. A composition according to claim 1 comprising at least 1% by weight of amethocaine, calculated as the free base.

8. A composition according to claim 1 comprising not more than 10% by weight of amethocaine, calculated as the free base.

9. A process for the preparation of a percutaneous anaesthetic composition according to claim 1 comprising mixing together amethocaine free base, gelling agent and a pharmacologically acceptable salt and maintaining the pH of the mixture at pH of not less than pH 7.0.

10. A percutaneous composition comprising amethocaine free base, an aqueous gelling agent and from 1 to 30% by weight of a pharmaceutically acceptable salt having an alkali or alkaline earth metal cation, wherein the pH of the composition is not less than pH 7.0, in a sterilised and packaged form.

11. A composition according to claim 10 packaged in a dispenser.

12. A composition according to claim 11 wherein the dispenser is a tube.

13. A composition according to claim 10 wherein the packaged form comprises a skin-conformable backing layer having on its skin facing surface a skin contacting layer of the anaesthetic composition.

14. A composition according to claim 13 wherein the layer of anaesthetic is inset from the edges of the backing layer and wherein the skin-facing surface of the backing layer not bearing the anaesthetic layer has a layer of adhesive thereon.

* * * * *